United States Patent [19]

Nomura

[11] 4,331,163

[45] May 25, 1982

[54] MEDICAL TREATMENT GLASSES

[76] Inventor: Haruo Nomura, 9-14, Kumata 8-chome, Higashi-sumiyoshi-ku, Osaka, Japan

[21] Appl. No.: 177,090

[22] Filed: Aug. 11, 1980

[51] Int. Cl.³ .............................................. A61N 1/18
[52] U.S. Cl. .................................................... 128/793
[58] Field of Search ............................... 128/791–793, 128/799, 802, 803, 380

[56] References Cited

U.S. PATENT DOCUMENTS 3,376,870  4/1968  Yamamoto .......................... 128/793
3,612,061  10/1971  Collins ................................. 128/799
3,709,228  1/1973  Barker ................................. 128/791

FOREIGN PATENT DOCUMENTS 1489708  5/1969  Fed. Rep. of Germany ...... 128/793

Primary Examiner—Lee S. Cohen
Attorney, Agent, or Firm—Armstrong, Nikaido, Marmelstein & Kubovcik

[57] ABSTRACT

Glasses for providing an effective medical treatment for false nearsightedness by giving an electric stimulation to effective locations on the face for stimulation therapy through plural electrodes attached to conductors laid on the rim and bows of the glasses. Each of the electrodes flexibly protrudes inwards from the rim and bows of glasses and movably supports an almost spherical piece thereon.

5 Claims, 3 Drawing Figures

MEDICAL TREATMENT GLASSES

BACKGROUND OF THE INVENTION

This invention relates to medical treatment glasses. More particularly, the invention is directed to glasses for treating false nearsightedness with electric stimulation.

A conventional stimulation therapy for false nearsightedness exists whereby electric conductors or electrodes such as small pieces of metal foil or small spherical metal units are attached, by adhesives, to prescribed effective locations on the body for stimulation therapy. Then, low-frequency electric current is carried from an oscillator to those locations through the small electric conductors, thereby giving an electric stimulation to those locations.

The conventional stimulation therapy is disadvantageous in that a search for the effective locations for the therapy is required and the conductors must be attached to each of the locations every time the therapy is applied.

SUMMARY OF THE INVENTION

The glasses of this invention which overcome the abovediscussed disadvantages of the prior art, relates to medical treatment glasses for false nearsightedness comprising:

(1) a pair of electric conductors laid on the bows and the rim of the glasses in a manner that they substantially surround the pair of lenses of the glasses, (2) a first series of plural electrodes attached to given portions of one of the conductors; each of the electrodes being of a semicircular spring, flexibly protruding inwards from the bows and rim of the glasses, and movably supporting an almost spherical piece, (3) a second series of plural electrodes attached to given portion of the other of the conductors; each of the electrodes being of a semicircular spring, flexibly protruding inwards from the bows and rim of the glasses, and movably supporting an almost spherical piece, (4) a first electric terminal protruding outward from one of the conductors through the bow of the glasses, and (5) a second electric terminal protruding outward from the other conductor through the bow of the glasses.

Thus, the invention describes herein makes possible the objectives of (a) easy and ready positioning each of the electrodes at the position corresponding to the effective locations of individual patients and (b) automatically pressing of each of the electrodes with proper pressure against the effective locations of each patient, thereby curing the fatigue and treating the false nearsightedness of the patient through electric stimulation sent to the electrodes.

BRIEF DESCRIPTION OF THE DRAWINGS

This invention may be better understood and its numerous objectives and advantages will become apparent to those skilled in the art by reference to the accompanying drawings as follows.

DESCRIPTION OF THE PREFERRED EMBODIMENTS

Figure 1:
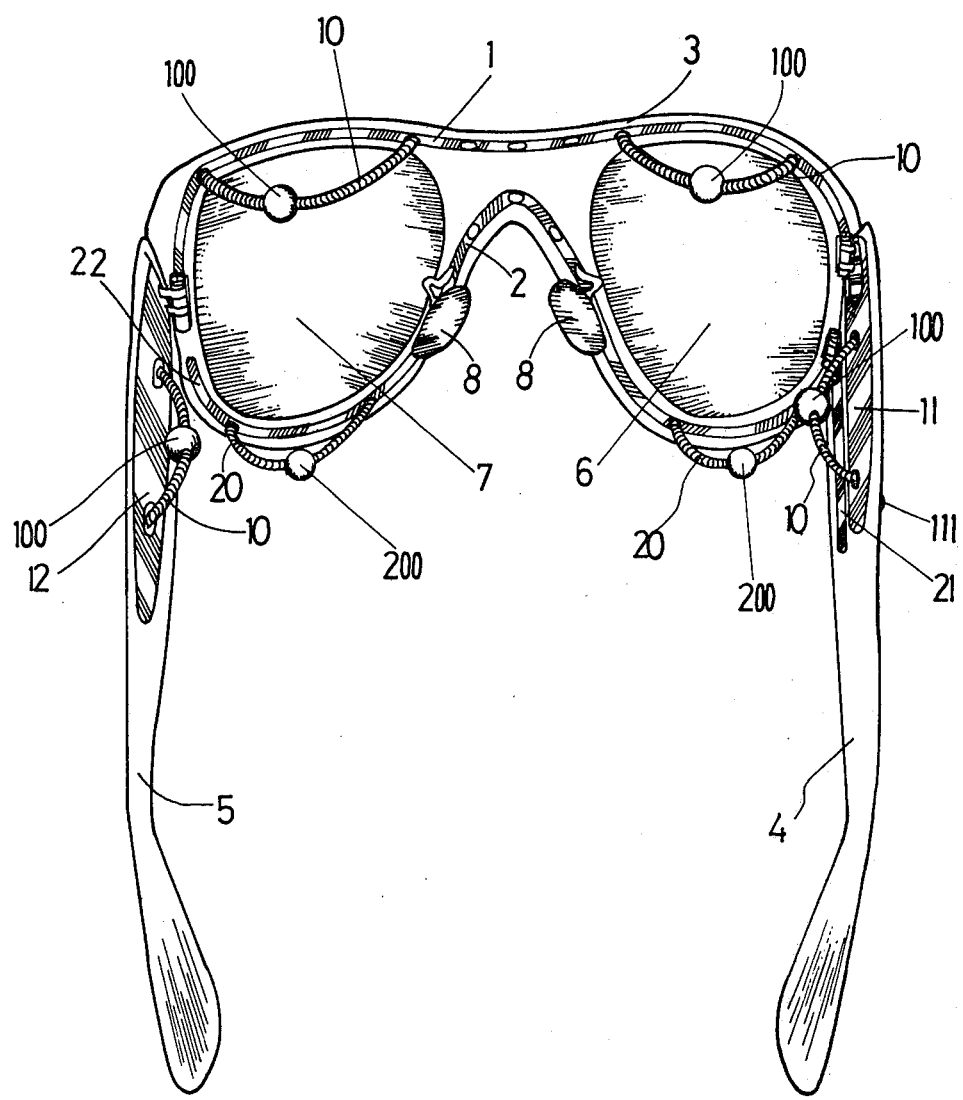
FIG. 1 is a perspective view of the medical treatment glasses of this invention.
Figure 2:
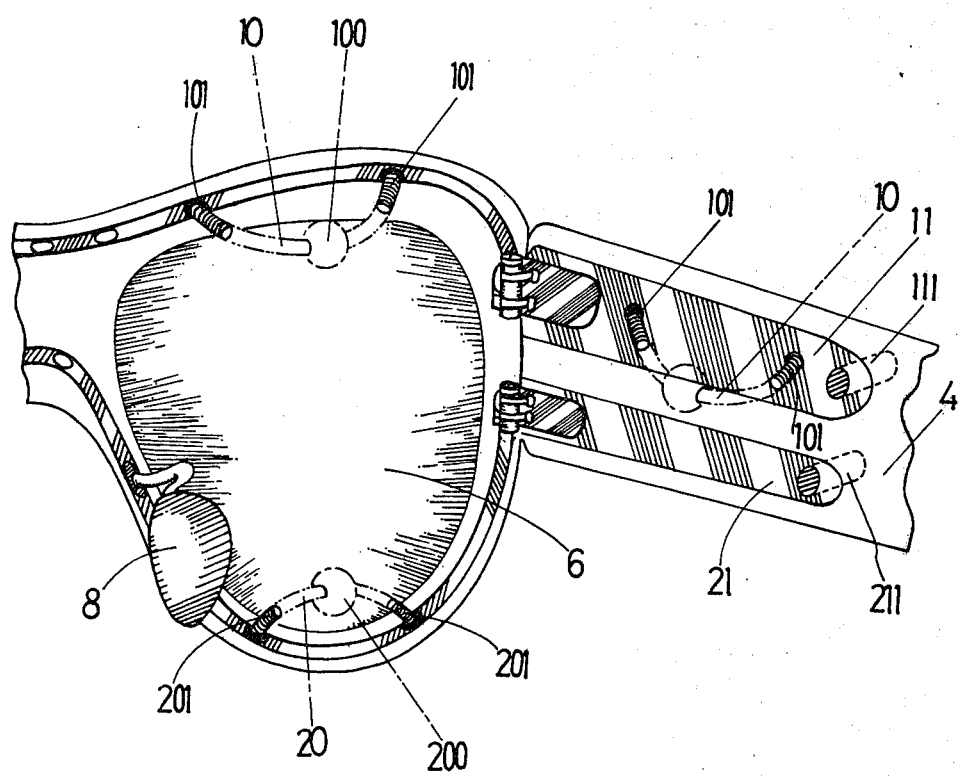
FIG. 2 is a partial perspective view showing the right part of the glasses of this invention.
Figure 3:
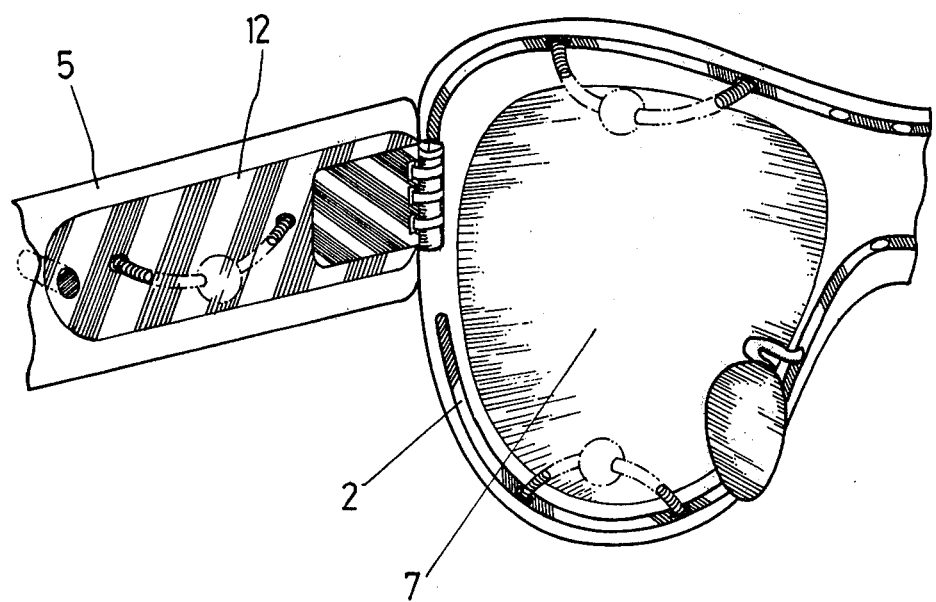
FIG. 3 is a partial perspective view showing the left part of the glasses of this invention.

The medical treatment glasses of this invention has a pair of electric conductors 1 & 2. Those conductors are laid on the rim 3 of the glasses. One end 11 of the conductors 1 extends to the bow 4 of the glasses and constitutes a support for the first electric terminal 111. The other end 12 of the conductor 1 extends to the other bow 5 of the glasses. One end 21 of the other conductor 2 also extends to the bow 4 and constitutes a support for a second electric terminal 211. The other end 22 of the conductor 22 ends near the bow 5 adjacent to the rim 3 and does not contact the conductor 1. Thus, those conductors are laid on the rim 3 of the glass in a manner that they substantially surround the pair of lenses 6 & 7 of the glasses. Both terminals 111 & 211 which are supported by the end portions 11 & 21 of the conductors 1 & 2, respectively, protrude outward from the bow 4, and are connected to a low-frequency electric current oscillator (not shown in any drawing).

The conductor 1 is provided with plural electrodes 10 at the specified portions which usually correspond to effective locations for electric stimulation treatment. Each of the electrodes 10 is of a semicircular spring and flexibly protrudes inwards from the rim 3 and the bows 4 & 5, thereby pressing the electrode under proper spring pressure against each of the effective locations on face while the glasses are worn. The electrode 10 usually has a almost spherical piece 100, which is movable on the electrode 10, in order to effectively contact the most effective location for each individual patient. The spherical piece 100 may be an electrically conductive material such as a metal, preferably covered by cloth, a conductive resin and a conductive gum containing metal powder or carbon powder. The electrode 10 may be attached to the bows and the rim at its both ends by means of pins 101.

The conductor 2 is likewise provided with plural electrodes 20 at the specified portions which usually correspond to effective locations for electric stimulation treatment. Each of the electrodes 20 is likewise of a semicircular spring and flexibly protrudes inwards from the rim 3, thereby pressing each electrode under proper spring pressure against each of the effective locations on face while the glasses are worn. Each electrode 20 usually has a spherical piece 200 which is of the same construction as the electrode 10. The electrode 20 may be also attached to the rim at its both ends by means of pins 201. Electrodes similar to electrodes 20 may be utilized in place of the conventional nose-supporting means 8 & 8, which contact the nose while the glasses are worn.

In using these glasses, each of the spherical pieces 100 & 200 is properly positioned to correspond to the predetermined locations on the face and the oscillator is connected to the terminals 111 & 211, and thereafter, the glasses are worn. Upon switching on the oscillator, low-frequency electric current flows to the spherical pieces 100 & 200 through the electrodes 10 & 20 and gives electric stimulation to those locations.

I claim:

1. A medical treatment glasses comprising:
    a pair of glasses including a pair of lenses, rims surrounding the lenses, and a pair of bows extending in one direction from the rims perpendicular to the lenses, a pair of electric conductors laid on the bows and the rim of said glasses in a manner that they substantially surround the pair of lenses of said glasses, a first series of plural electrodes attached to given portions of one of said conductors; each of said electrodes comprising a semicircular spring, flexibly protruding inwards from the bows and rim of said glasses, and an almost spherical piece movably supported on the spring, a second series of plural electrodes attached to given portions of the other of said conductors; each of said electrodes comprising a semicircular spring, flexibly protruding inwards from the bows and rim of said glasses, and an almost spherical piece movably supported on the spring, a first electric terminal protruding outward from one of said conductors through one of the bows of said glasses, and a second electric terminal protruding outward from the other conductor through said one bow of said glasses.

2. Medical treatment glasses, according to claim 1, wherein said spherical piece is of a metal.

3. Medical treatment glasses, according to claim 1, wherein said spherical piece is of a conductive resin.

4. Medical treatment glasses, according to claim 1, wherein said spherical piece is of a conductive gum.

5. Medical treatment glasses, according to claim 2, wherein said spherical piece is covered by cloth.

* * * * *